US006058331A

United States Patent [19]
King

[11] Patent Number: 6,058,331
[45] Date of Patent: May 2, 2000

[54] APPARATUS AND METHOD FOR TREATING PERIPHERAL VASCULAR DISEASE AND ORGAN ISCHEMIA BY ELECTRICAL STIMULATION WITH CLOSED LOOP FEEDBACK CONTROL

[75] Inventor: Gary W. King, Findley, Minn.

[73] Assignee: Medtronic, Inc., Minneapolis, Minn.

[21] Appl. No.: 09/067,050

[22] Filed: Apr. 27, 1998

[51] Int. Cl.$^7$ .................................................. A61N 1/36
[52] U.S. Cl. .................................. 607/62; 607/2
[58] Field of Search .................................. 607/62, 46, 2, 607/43, 44, 48, 50, 51, 52, 59, 60, 63, 116, 117, 118

[56] References Cited

U.S. PATENT DOCUMENTS

| | | | |
|---|---|---|---|
| 3,650,277 | 3/1972 | Sjostrand et al. | 128/419 |
| 5,031,618 | 7/1991 | Mullett | 128/421 |
| 5,058,584 | 10/1991 | Bourgeois | 607/46 |
| 5,199,428 | 4/1993 | Obel et al. | 607/44 |
| 5,293,879 | 3/1994 | Vonk et al. | 128/782 |
| 5,342,409 | 8/1994 | Mullett | 607/46 |
| 5,623,937 | 4/1997 | Sasaki | 128/708 |
| 5,702,429 | 12/1997 | King | 607/46 |
| 5,707,400 | 1/1998 | Terry, Jr. et al. | 607/44 |
| 5,718,721 | 2/1998 | Ross | 607/46 |

FOREIGN PATENT DOCUMENTS

| | | | |
|---|---|---|---|
| 95/17921 | 7/1995 | WIPO | A61N 1/00 |

OTHER PUBLICATIONS

PCT Search Report Jul. 27, 1999 PCT/ISA.

Takahashi, Nomura, Tomita, Matsumoto, "Effects of Peripheral Nerve Stimulation on the Blood Flow of the Spinal Cord and the Nerve Root," *Spine* 13(11):1278–83 (Nov. 1988).

Kaada, "Vasodilation induce by transcutaneous nerve stimulation in peripheral ischemia Raynaud's phenomenon and diabetic polyneuropathy," *The European Society of Cardiology* (Copyright 1982) 303–314.

Cameron, Cotter, Robertson, Maxfield, "Nerve function in experimental diabetes in rats: effects of electrical stimulation," *American Journal of Physiology: Endocrinology and Metabolism*, (Feb. 1993) vol. 27, No. 2.

Sugimoto, Manafo, Shimazaki, "Regional sciatic nerve blood flow response to limb movement," *The American Physiological Society*, (Copyright 1987) H439–H441.

Holdaas, DiBona, "Stimulatory and inhibitory reflexes from somatic receptors: effect on renin release," *American Journal of Physiology: Regulatory, Integrative and Comparative Physiology*, R1005–R1010, vol. 15, No. 6, (Jun. 1984).

Monafo, Eliasson, Shimazaki, Sugimoto, "Regional Blood Flow in Resting and Stimulated Sciatic Nerve of Diabetic Rats," *Experimental Neurology* 99, 607 (1988)pp. 607–615.

Kobrine, Evans, "The Effect Of Sciatic Nerve Stimulation On Spinal Cord Blood Flow," *Journal of the Neurological Sciences* (1978) 38:435–439.

Rigaux, "Influence De La Frequence De Stimulation Neuromusculaire Electrique De La Jambe Sur Le Debit Arterial Femoral," *Journal des Maladies Vascularize* (Paris), 1995, 20, 9–13.

Loubser, "Abstracts of the 3rd International Symposium", *Acupuncture & Electro–Therapeutics Res*, vol. 12, No. 3 & 4, (1987).

Eriksson, Mannheimer, "The Effect of Transcutaneous Electric Nerve Stimulation on Ischemic Pain in the Lower Extremities", *Clinic !*, Vasa Hospital, Gothenburg, pp. 33–35 (1980).

Jivegard, Augustinsson, Holm, Risberg, Ortenwall, "The Effects of Spinal Cord Stimulating (SCS) in Patients with Inoperable Severe Lower Limb Ischaemia: A Prospective Radomized Controlled Study," *Eur J Vase Endovasc Surg*, 421–425 (1995).

Horsch, claeys, "Spinal cord stimulation for ischemic rest pain,"*The Belgian randomized stud*, (1994), pp. 197–201.

Kumar, Toth, Nath, Verma, Burgess, "Improvement of limb circulation in peripheral vascular disease using epidural spinal cord stimulation: a prospective study," *J. Neurosurg*, vol. 86, (Apr. 1997).

Gersbach, Hasdemir, Stevens, Nachbur, Mahler,"Discriminative Microcirculatory Screening of Patients with Refractory Limb Ischaemia for Dorsal Column Stimulation," *Eur J. Vasc Endovasc Surg*, vol. 13, (May 1997).

Rickman, Wuebbels, Holloway, "Spinal cord stimulation for relief of ischemic pain in end–stage arterial oculusive disease," *Journal of Vascular Nursing*, pp. 14–20, (Mar. 1994).

Bunt, Holloway, Robey, Malone, "Dorsal Column Stimulation Delays Amputation In Some Patients With Ischemic Rst Pain and Ischemic Tissue Loss," Abstract: The Western Vascular Surg., Society Meeting, (Jan. 1994).

Kepplinger, Pernak, Ray, Schmid, "Pain Clinical Aspects and Therapeutical Issues Part II," *Edition Selva Verlag Linz*, (1993).

Ross, Perumbeti, Mazala, Motley–Matson, Macko, "Spinal Cord Stimulation for Ischemic Pain in Endstage Peripheral Vascular Disease," *American Academy of Pain Management*, (1992).

Galley, Illis, Krainick, Meglio, Sier, Staal, "First International Congress," *International Neuromodulation Society*, (May 1992).

(List continued on next page.)

*Primary Examiner*—Kennedy J. Schaetzle
*Attorney, Agent, or Firm*—Banner & Witcoff, Ltd.

[57] ABSTRACT

The present invention discloses techniques for therapeutically treating peripheral vascular disease. A sensor is implemented for sensing the extent of blood flow in a patient's limb or ischemic pain and generating a corresponding sensor signal. The signal is processed to determine the level of spinal cord stimulation or peripheral nerve stimulation to be applied. This information is provided to a signal generator which thereby provides electrical stimulation energy to one or more stimulation leads. Stimulation of the spinal cord, peripheral nerve or neural tissue ganglia thereby improves blood flow, helps restore tissue health and reduces the extent of ischemic pain in the limbs of a PVD patient or organs of other patients. The present invention thereby allows the stimulation to be adjusted automatically to account for changing conditions of the patient throughout the day.

47 Claims, 8 Drawing Sheets

OTHER PUBLICATIONS

Croom, Barron, Chandler, Foreman "Changes in Skin Blood Flow In Rat hindpaw During Dorsal Column Stimulation," *Experimental Biology*, (1993).

Bunt, Holloway, Lawarence, Cherney, Malone, "Experience with Epidural Spinal Stimulation in the Treatment of End--Stage Peripheral Vascular Disease," Seminars in Vascular Surgery, vol. 14, No. 4, pp. 216–220 (Dec. 1991).

Ubbink, Tulevski, den Hartog, Koelemay, Legemat, Jacobs, "The Value of Non–invasive Techniques of the Assessment of Critical Limb Ischaemia," *Eur J. Vase Enovasc*, Surg. 13, 296–300 (1997).

Linderoth, Fedorcsak, Meyerson, "Is Vasodilatation Following Dorsal Column Stimulation Mediated by Antidromic Activation of Small Diameter Afferent," *Acta Neurochirurgical*, Suppl 46, 99–101 (1989).

Croom, Foreman, Chandler, Koss, Barron, "Role of Nitric Oxide in Cutaneous Blood Flow Increased in the Rat Hindpaw during Dorsal Column Stimulation," *Neurosurgery*, vol. 40, No. 3, (Mar. 1997).

Croom, Barron, Chandlr, Foreman, "Cutaneous blood flow increase in the rat hindpaw during dorsal column stimulation," *Brain Research*, 738, pp. 281–286 (1996).

Linderoth, Fedorcsak, Bjorn, Meyerson, "Peripheral Vasodilation after Spinal Cord Stimulation" Animal Studies of Putative Effetor Mechanisms, *Neurosurgery*, vol. 28, No. 2, (1991).

Linderoth, Gumasekera, Bjorn, Meyerson, "Effects of Sympathectomy on Skin and Muscle Microcirculation during Dorsal Column Stimulation: Animal Studies," *Neurosurgery*, vol. 29, No. 6, (1991).

Linderoth, Herregodts, Meyerson, "Sympathetic Mediation of Peripheral Vasodilation Induced by Spinal Cord Stimulation: Animal Studies of the Role of Cholinergic and Adrenergic Receptor Subtypes," *Experimental Studies, Neurosurgery*, vol. 35, No. 4, (Oct. 1994).

Linderoth, Stiller, Gunasekera, O'Connor, Ungerstedt, Brodin, "Gamma–aminobutyric Acid is Released in the Dorsal Horn by Electrical Spinal Cord Stimulation" An In Vivo Microdialysis Study in the Rat, Neurosurgery, vol. 34, No. 3, (Mar. 1994).

APPARATUS AND METHOD FOR TREATING PERIPHERAL VASCULAR DISEASE AND ORGAN ISCHEMIA BY ELECTRICAL STIMULATION WITH CLOSED LOOP FEEDBACK CONTROL

BACKGROUND OF THE INVENTION

1. Field of the Invention

This invention relates to techniques for treating symptoms of peripheral vascular disease and organ ischemia, and more particularly relates to techniques for improving blood flow to ischemic limbs and organs using spinal cord or peripheral nerve stimulation.

2. Description of Related Art

A large number of humans suffer from peripheral vascular disease (PVD). PVD refers to a condition that adversely affects blood flow in the limbs. PVD may be caused by a number of disorders with the body such as arteriosclerosis (with or without diabetes), Raynaud's disease (idiopathic vasospasms), Buerger's disease (thromboangiitis obliterans) or embolic occlusive disease. PVD causes poor blood flow to the limbs of the patient thereby causing ischemic pain in the arms or legs. There are several surgical techniques that may restore compromised blood flow, such as revascularization procedures or angioplasty, but these might not be appropriate, they might have already failed, or the patient might prefer to try less invasive therapy. Since ischemic pain is usually not responsive to narcotics, the patient has no available pain relief and must endure the pain. Poor blood flow also means reduced oxygen that is carried in the blood stream to cells. As oxygen falls to very low levels, cell death or necrosis can develop, leading to nonhealing lesions, gangrene and amputation. Skin oxygen level measured by tanscutaneous oximetry (TcPO2) is above 40 mm Hg and usually over 50 mm Hg for most normal human beings. PVD patients have much lower skin oxygen levels. If it is below 20 mm Hg, lesions will not heal. Below 10 mm Hg, tissue may deteriorate. When the blood flow reaches very low levels, the feet may hurt especially when the patient is lying down (rest pain). In this case, the limb blood supply may become critical (critical limb ischemia). If there is no solution to this pain, the patient may request that the limb be amputated.

In earlier stages of PVD, some ischemic pain does not come at rest (rest pain), but rather when the patient exercises. Called claudication pain, this type of pain is created in muscles which cannot get enough oxygen. Claudication pain can be elicited by the most basic physical activity such as walking. The patient will walk less and less and the cardiovascular system will further deteriorate. The quality of life for the patient thereby diminishes.

Clinical researchers have found that spinal cord stimulation (SCS) may be used to help improve blood flow and alleviate ischemic pain in limbs caused by poor blood flow due to peripheral vascular disease (PVD). SCS may reduce pain via the well known Gate Control Theory proposed by Ronald Melzack and Patrick Wall in 1965. There are also three probable mechanisms, based on animal and clinical research from SCS for PVD, of how SCS can improve blood flow: (1) inhibition of excess sympathetic nervous activity due to pain; (2) further inhibition of sympathetic nervous background tone; and (3) release of vasoactive substances in the limb. Normally the sympathetic nervous system controls peripheral blood flow. The sympathetic nervous system is able to contract the small precapillary smooth muscle sphincters that adjust local blood flow. During times of stress or vigorous activity, there is high sympathetic tone, and blood is shunted from the distal limbs to large proximal muscles. Pain in the periphery can also increase the sympathetic outflow and cause such shunting. Ironically, in the elderly person with PVD, the pain of limb ischemia can trigger more sympathetic outflow, and further decrease blood supply to distal limb areas. Researchers have studied the role of the sympathetic system in producing ischemia using rats and have shown that interventions that inhibit the sympathetic outflow like drugs or sympathetic ganglia destruction (sympathectomy) can dramatically increase vasodilation in the periphery. They have also shown in rats that SCS can recruit A-delta nerve fibers in dorsal roots (normally carrying pain messages). Antidromic actions potentials in these fibers travel to the distal limb parts and release CGRP and NO, molecules which greatly assist local vasodilation. Both of these effects may be present in humans getting SCS for their PVD, and depending upon the precise parameters of stimulation, may explain the mechanism for the benefit of vasodilation.

Typically during SCS for ischemic feet or legs, an epidural lead (such as the Medtronic, Inc., PISCES® or RESUME® lead) is placed to stimulate the spinal cord near the midline of the dorsal columns at T8-L1. This stimulation provides strong paresthesia in the feet, and may inhibit sympathetic spinal centers in the distal part of the spinal cord or cause the release of vasoactive substances, as discussed above. For ischemic pain in the hands, a similar epidural lead is typically placed on the symptomatic side of the spinal cord around C5–C8. If hand ischemic pain is bilateral, a dual channel system (such as the Mattrix® system sold by Medtronic, Inc.) or two independent systems are used. Benefits of SCS beyond relief of ischemic pain have also been studied and used with clinical success, such as warming the feet, healing of small ulcers, increasing of walking distances and improving the chances to avoid amputation of parts of a foot or the entire foot.

For all humans, the degree of limb ischemia varies greatly during the day. For the PVD patient, it often reaches painful and dangerous levels (relative to tissue health). In endstage PVD. the ischemic pain is worse when lying down since gravity cannot help the blood flow. In earlier PVD, it begins with exercise due to muscles competing for blood flow. Ischemic pain may even increase in response to ingestion of certain foods or medicines. For instance, medicines that decrease heart output may also cause reduced blood flow in the extremities thereby increasing ischemic pain. In general, any activity or condition that increases the sympathetic nervous system output can also divert blood from extremities to more proximal muscles (fight or flee reflexes). For all of the above reasons, SCS may be an effective therapy to not only decrease pain, by also improve limb blood flow.

Present commercially available SCS systems, however, do not provide a technique for automatically varying levels of SCS to account for these changing daily conditions. Most commercially available SCS systems have continuous stimulation at one or two amplitudes for neuropathic pain, and perhaps automatically cycle "on" or "off", but not according to the degree of limb ischemia. U.S. Pat. No. 5,702,429 (King), assigned to Medtronic, Inc. of Minneapolis, Minn., provides an SCS system that uses closed loop feedback techniques to adjust the parameters of stimulation (voltage, pulse width, frequency, etc.) automatically so that the conscious sensation (called paresthesia) or the degree of pain relief can be kept constant, regardless of patient position or activity. However, this art is not designed to keep constant any of the beneficial vascular effects of SCS for the PVD patient.

It would be advantageous to be able to have the parameters of stimulation automatically adjusted to prevent uncomfortable or dangerous conditions from occurring. This would be useful during sleep, when a patient cannot adjust said parameters, and also during daily activities or patient positions, so that both ischemic pain relief and vascular improvement can be maintained optimally, without distraction of the patient.

Additionally, constant stimulation of the spinal cord may not be desirable since stimulation may not be necessary during times when ischemia has subsided, it may have bothersome or adverse side effects, or it may cause the body to build up a tolerance to the stimulation. With closed-loop feedback control, the patient would be more likely to rest better and to enjoy an active lifestyle, and not have to limit activities or medications. The patient may also be able to keep the amplitudes of stimulation higher, knowing that a situation will not develop which is unduly painfull or disadvantageous to health. Additionally, the patient may be able to walk and otherwise exercise more.

The present invention is therefore directed to overcoming the disadvantages of the foregoing SCS, and to provide a degree of vascular improvement (proportional to the degree of ischemia reduction) that is otherwise unobtainable.

SUMMARY OF THE INVENTION

As explained in more detail below, the present invention overcomes the above-noted and other shortcomings of prior techniques for treatment of blood flow and ischemic pain in PVD patients. The invention is useful for controlling electrical stimulation to provide adequate levels of blood flow in the limbs and sufficient reduction in ischemic pain. In a preferred embodiment, the present invention includes a sensor, a sensor signal processor, a signal generator, and one or more stimulation electrodes. The sensor monitors a characteristic of the patient's body indicative of the extent of blood flow or ischemic pain and generates a sensor signal. The sensor may be external or implanted. The sensor signal processor processes the sensor signal and provides a control signal to the signal generator. The signal generator generates in response to a control signal from the sensor signal processor a stimulation pulse having a predetermined pulse period, pulse width and amplitude. An implanted stimulation electrode delivers the pulse to precise locations in the spinal cord In alternative embodiments, the stimulation is provided to a peripheral nerve, such as a sciatic nerve, or to neuronal ganglia, such as the sympathetic chain. Blood flow is thereby improved in the limbs or organs and ischemic pain is reduced. By using the foregoing techniques, the level of electrical stimulation can be varied throughout the day to account for the patient's changing conditions and needs.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

The present invention discloses techniques for relieving ischemic pain and/or improving limb blood flow in patients with peripheral vascular disease (PVD). As preferred, the invention includes generally a sensor for monitoring the location or degree of certain physical conditions of a patient to determine the extent of ischemia being suffered, a signal processing portion for processing the sensed signals to recognize symptoms that may relate to ischemic pain or to tissue endangerment, and a therapy delivery portion for providing stimulation to improve blood flow to the limbs thereby reducing the pain suffered by the patient and reversing an undesirable tissue blood flow. While relief of ischemic pain is a valuable and deliberate object of the present invention, the invention also serves to maintain an adequate level of blood flow to the limbs.

Figure 1:
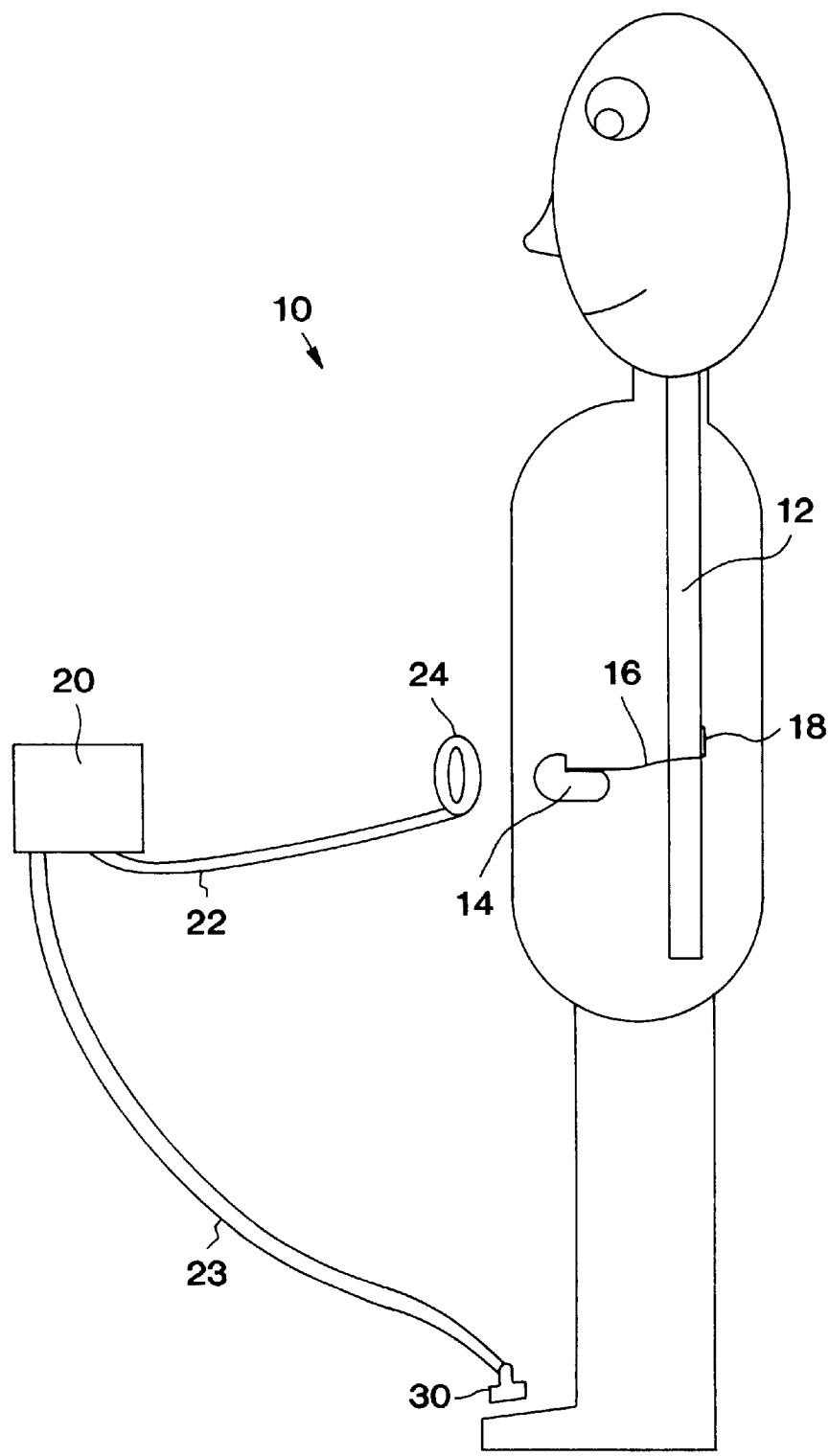
FIG. 1 is a diagrammatic illustration of a preferred embodiment of the present invention having an external sensor, a signal generator, a means of processing the sensed signal and controlling the signal generator and a stimulation lead implanted near the spinal cord.

Referring to FIG. 1, an SCS system or device 10 made in accordance with the preferred embodiment. The system includes generally a sensor 30, an implanted signal generator 14, an implanted extension 16 and one or more stimulation leads 18. Signal generator 14 may receive feedback instructions form an external component 20, which processes a recorded signal from sensor 30 and sends instruction to signal generator 14 via antenna 24. For SCS, the signal generator 14 is commonly implanted subcutaneously in a human body on the abdomen or back but for peripheral nerve stimulation (discussed herein) it may be implanted subcutaneously in one limb. Signal generator 14 may take the form of a modified signal generator like Model 7424 manufactured by Medtronic, Inc. under the trademark Itrel® or it might have no battery and instead get programming signals and energy from a modified exterior transmitter 20 and antenna 24 like a radio frequency system manufactured by Medtronic, Inc. known as X-trel® or Mattrix®, which are incorporated by reference. As preferred, signal generator 14 provides electrical stimulation by way of pulses although other forms of stimulation may be used such as continuous electrical stimulation.

Lead 18 is positioned to stimulate a specific site in the spinal cord or, alternatively, may be positioned along a peripheral nerve or adjacent neural tissue ganglia like the sympathetic chain. If the spinal cord is to be stimulated, lead 18 may have electrodes that are epidural, intrathecal or placed into the spinal cord itself Effective spinal cord stimulation may be achieved by any of these lead placements. Lead 18 may take the form of any of the leads sold for stimulating the spinal cord or peripheral nerve and is coupled to signal generator 14 by a conventional conductor or extension 16. Lead 18 may be a paddle having a plurality of electrodes including, for example, a Medtronic paddle having model number 3587A. Those skilled in the art will appreciate that any variety of leads to stimulate the spinal cord may be used to practice the present invention. Commonly, if lead 18 has epidural electrodes, these will be positioned at spinal vertebral levels T8-L1, with the maximum increases in limb blood flow often found from T10-L1 where major nerve pathways to the lumbar ganglia important for autonomic control of the limb blood flow may be found. Often, at T11-L1, the electrodes may be placed over the physiological midline of the spinal cord, delivering paresthesia into both feet and helping blood flow in both feet. Other spinal levels may also help blood flow to the feet. To control the blood flow to the hands, the electrodes may be placed epidurally at spinal vertebral levels C4–C8. Lead 18 may also be positioned adjacent to the lumbar sympathetic ganglia. Activity in neurons in these ganglia (T12-L5 for legs; T1–T3 for arms) is able to activate afferent sympathetic nerves that control blood flow. Stimulation to inhibit these neurons can prevent sympathetic nerve action potentials that are normally able to constrict blood vessels, thereby decreasing tissue blood flow.

External sensor 30 is placed very near or on the patient's skin with a strap or elastic bandage over the limb of interest to sense a characteristic which is indicative of ischemia exhibited by the patient. Correlates for measuring ischemia include, for example, skin oxygen ($TcPO_2$), skin blood oxygen saturation or skin temperature. These correlates may be measured with an external, noninvasive sensor. Such a sensor 30 may be a digital clamp/probes for monitoring blood oxygen saturation. Alternatively, sensor 30 may monitor skin temperature (skin probe), measure equilibrium levels of oxygen in the skin ($TcPO_2$ probe), measure oxygen saturation levels in the blood (blood saturation monitor), or measure Doppler shifts of moving blood cells (laser Doppler probe). The preferred probe measures temperature because, like instruments commonly used for patients in clinics, it can be inexpensive, easily replaced and durable. $TcPO_2$ often requires heating of a portion of the skin to near painful levels (44 degrees Celsius or more) and an airtight seal using an adhesive disk or fluid (Model TCM3-3 by Radiometer, Inc.). These are expensive and prone to dislocation and technique errors. Laser Doppler probes are useful, but tend to measure blood flow in very small skin volumes and are very prone to movement artifacts. Although easy to dislocate, blood saturation monitors may also be useful such as a small device that holds a single toe or finger. A possible source of error in measuring the skin blood flow involves the physiological process of shunting a major portion of blood flow through the skin to regulate body temperature. As described above, external sensors are best used when the patient is sedate, and not having great physical motion. This could be when done when the patient is sitting, lying down or sleeping.

External sensor 30 may also monitor the level of activity of the patient For example, sensor 30 may be an accelerometer implanted for monitoring the degree of vigorous motion of a limb such as during walking. Sensor 30 may also be a motion detector carried anywhere on the patient's body, even in a pocket. For example, sensor 30 may sense three-dimensional or two-dimensional motion (linear rotational or joint motion), such as by an accelerometer. One such sensor suitable for use with the present invention is described in U.S. Pat. No. 5,293,879 (Vonk).

Figure 2:
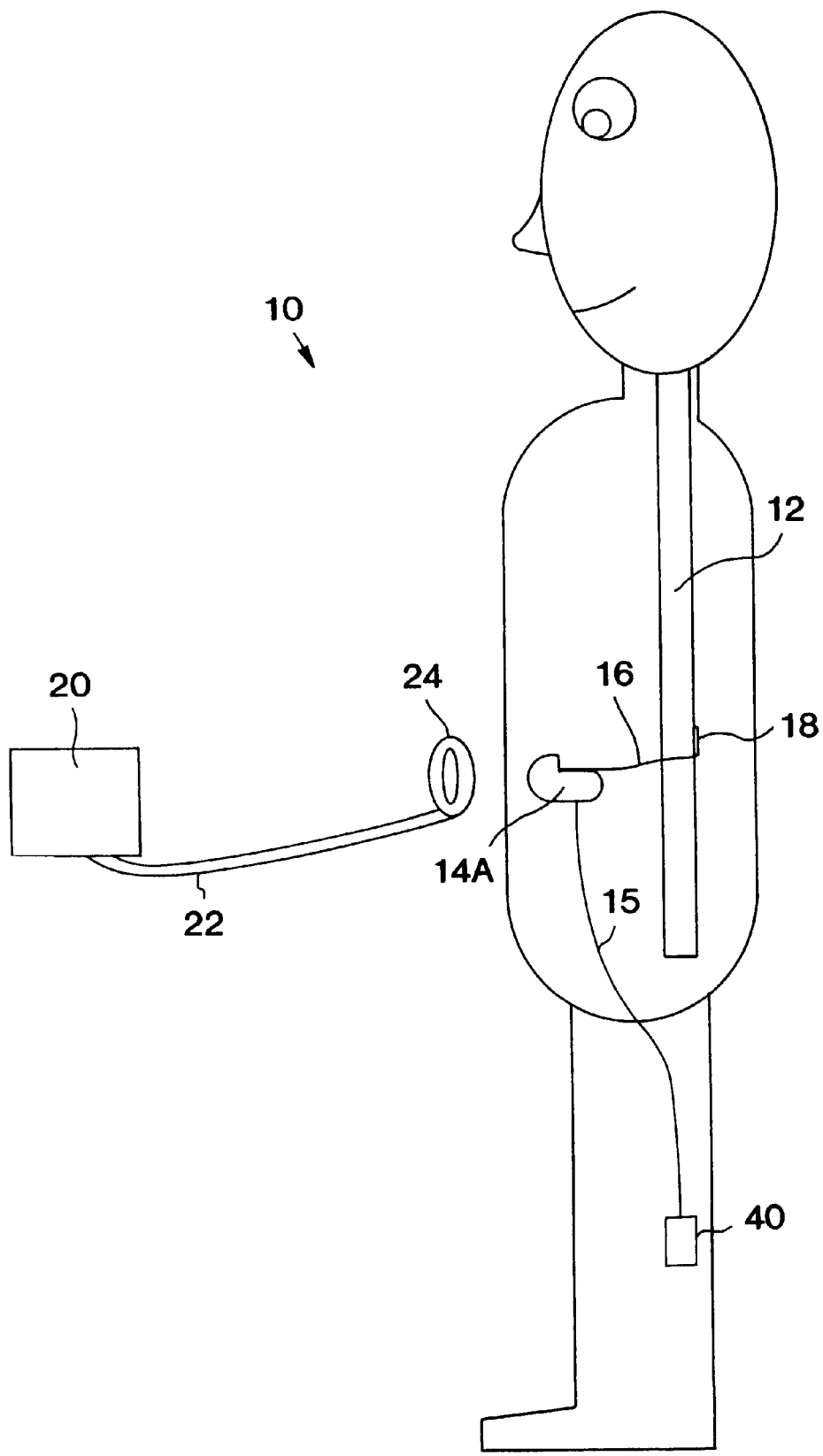
FIG. 2 is a diagrammatic illustration of a preferred embodiment of the present invention having an internal sensor, a signal generator, a means of controlling the signal generator and a stimulation lead implanted near the spinal cord.

In another embodiment as shown in FIG. 2, the sensor 40 is implanted under the skin or inside the muscle of a limb, and may be directly connected inside the patient via an extension 15 to a complex signal generator 14A which also processes the information from the sensor 40 and contains software to decide the best response. If implanted, sensor 40 may be suited to pick up a signal from a limb and send it back to the signal generator 14A via internal cable 15. In this embodiment signal generator 14A has an algorithm and signal processing subcomponents to control the output of the signal generator 14A. External controller 20 may be used to give instructions to signal generator 14A by means of radio frequency uplink and downlink through antenna 24.

Internal sensor 40 is placed under the patient's skin, in or near muscles groups, or along a nerve or artery. It would be used to sense a characteristic which is indicative of ischemia or impending ischemia exhibited by the patient. Correlates for measuring ischemia include, for example, skin oxygen level, muscle oxygen level, tissue temperature, muscle lactic acid build-up, muscle activity, motion or acceleration, blood flow to the limb, or nerve activity to the muscles and joints that correlates with limb usage.

Internal sensor 40 may also be a suitable accelerometer, such as those found in pacemakers manufactured by Medtronic, Inc. and described in patent application Ser. No. 08/399,072 filed Mar. 8, 1995, in the names of James Sikorski and Larry R. Larson and entitled "Package Integrated Accelerometer" now U.S. Pat. No. 5,674,258.

Alternatively, external sensor 30 or internal sensor 40 may detect muscle electromyographic activity EMG) in one, two or more muscles, or in reciprocal muscles at one joint. For such detection, sensor 30 may take the form of a recording electrode held by conductive adhesive to the skin over a muscle of interest. Brain electro-encephalographic activity (EEG) (e.g., motor cortex potentials recorded above the precentral gyrus motor neurons controlling specific muscle groups) also may be detected by internal sensor 40. For direct monitoring of sympathetic nerve activity, internal sensor 40 may record from neurons in sympathetic ganglia or along the intrinsic neurons found on the outside of major arteries. It may even sense physiological changes in major organs that have consisting responses to elevated sympathetic nervous system outflow, such as the heart rate or blood pressure.

Internal sensor 40 may be a sensory recording electrode for monitoring sensory signals that are caused by motion. It may be located at the dorsal roots or peripheral nerves.

Sensor 30 or 40 also may be capable of detecting gravity direction or motion relative to some object (e.g., a magnet) either implanted or fixed nearby. For example, U.S. Pat. No. 5,031,618 (Mullet) ("the '618 patent) discloses such a sensor. In this case, when a patient lies flat with feet upon the bed, the amplitude of stimulation may be adjusted, not to directly affect paresthesia and pain relief as cited by the '618 patent, but rather to keep blood flow in the limb at a preferred level. Sensor 30 or 40 may also include a device capable of detecting nerve compound action potentials (e.g. either sensory afferent information from muscle or skin receptors or efferent motor potentials controlling a muscle of interest). They might also detect changes in the length of one or more muscles.

Alternatively, two or more different types of sensors may be implemented. For example, the present invention may utilize an oxygen sensor along with a motion sensor. In this case, the oxygen sensor may sense ischemia in the muscles to determine the amount of stimulation. The motion sensor senses whether the patient is engaged in physical exertion such that the lower levels of oxygen in the muscles would not indicate ischemia but simply rather physical exertion. In this case, stimulation may not be required. Those skilled in the art will appreciate that any number of sensors may be utilized to sense indicia of blood flow ischemia and are covered within the scope of the present invention.

Figure 3:
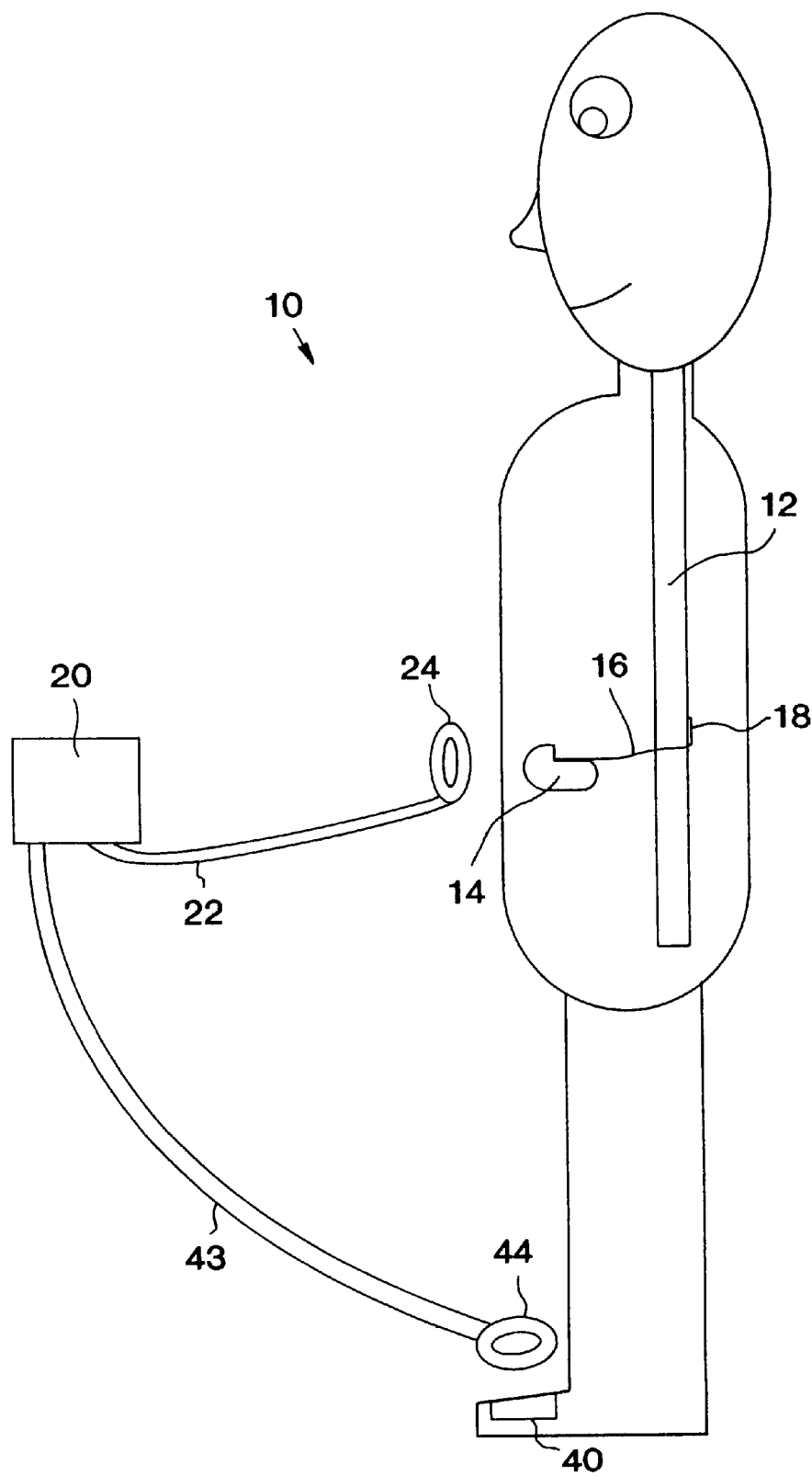
FIG. 3 is a diagrammatic illustration of a preferred embodiment of the present invention having an internal sensor, a signal generator, a means of picking up a sensed signal and controlling the signal generator, and a stimulation lead implanted near the spinal cord.

FIG. 3 discloses another embodiment of the present invention utilizing an internal sensor 40 and a receiver 44 for telemetrically receiving the sensed signal. Receiver 44 transports the sensed signal back to the external component 20 via lead 43. Instructions are then sent to signal generator 14 via antenna 24.

As an alternative to SCS, peripheral nerve stimulation (PNS) can also be used to help alleviate neuropathic pain by placing a group of electrodes to stimulate nerve parts that are proximal to the site of a nerve disorder. In accordance with the present invention, PNS may be performed on the sciatic nerve. PNS on one nerve might reduce ischemic pain and/or increase blood flow in the area of nerve distribution more than that possible from SCS.

Figure 4:
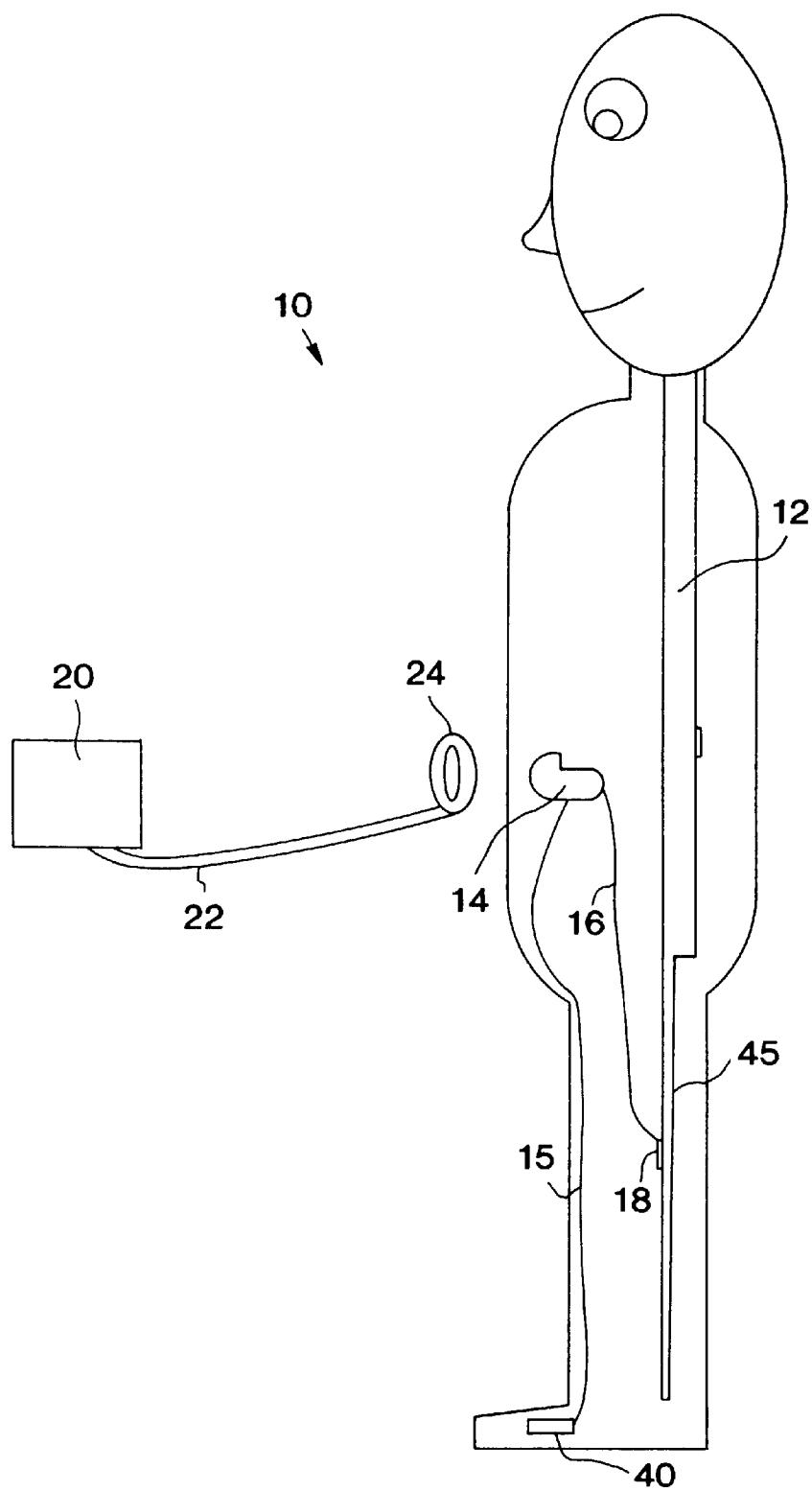
FIG. 4 is a diagrammatic illustration of a preferred embodiment of the present invention having an internal sensor, a signal generator, a means of processing the sensed signal and controlling the signal generator and a stimulation lead implanted near a peripheral nerve.

FIG. 4 is a drawing of another embodiment of the present invention where ischemic pain may be treated by stimulation of a sciatic or arm nerve. In this embodiment, lead 18 is positioned to provide stimulation to a sciatic nerve 45. Lead 18 may be implanted, for example, during leg vascular by-pass surgery. Signal generator 14 may be placed near the abdomen or back or on the most symptomatic limb near implantable sensor 40. Alternatively, signal generator 14 and lead 18 may be enclosed as a single device component near sciatic nerve 45. Alternatively, two or more leads may be placed at sciatic nerves in both legs. Although sensor 40 is preferably placed to sense conditions of the same limb as that in which the sciatic nerve is being stimulated, sensor 40 may be placed in any other location described above as well.

In certain circumstances, a physiologically more coordinated response, especially of sympathetic outflow inhibition, might be desired. In such a case, SCS may be used in combination with PNS. In yet another embodiment, the present invention may provide stimulation of the sympathetic neuronal ganglia or sympathetic neurons to provide the desired therapy. In addition, any combination of SCS, PNS, sympathetic neuronal ganglia stimulation and sympathetic neuron stimulation may be used. As other applications, the present invention may be utilized to improve blood flow in other parts of the body in addition to the limbs including, for example, human organs. The present invention may also be used to prevent tissue degeneration, maintain a constant tissue blood flow, relieve ischemic pain, treat ulcers, or any combination thereof.

Figure 5:
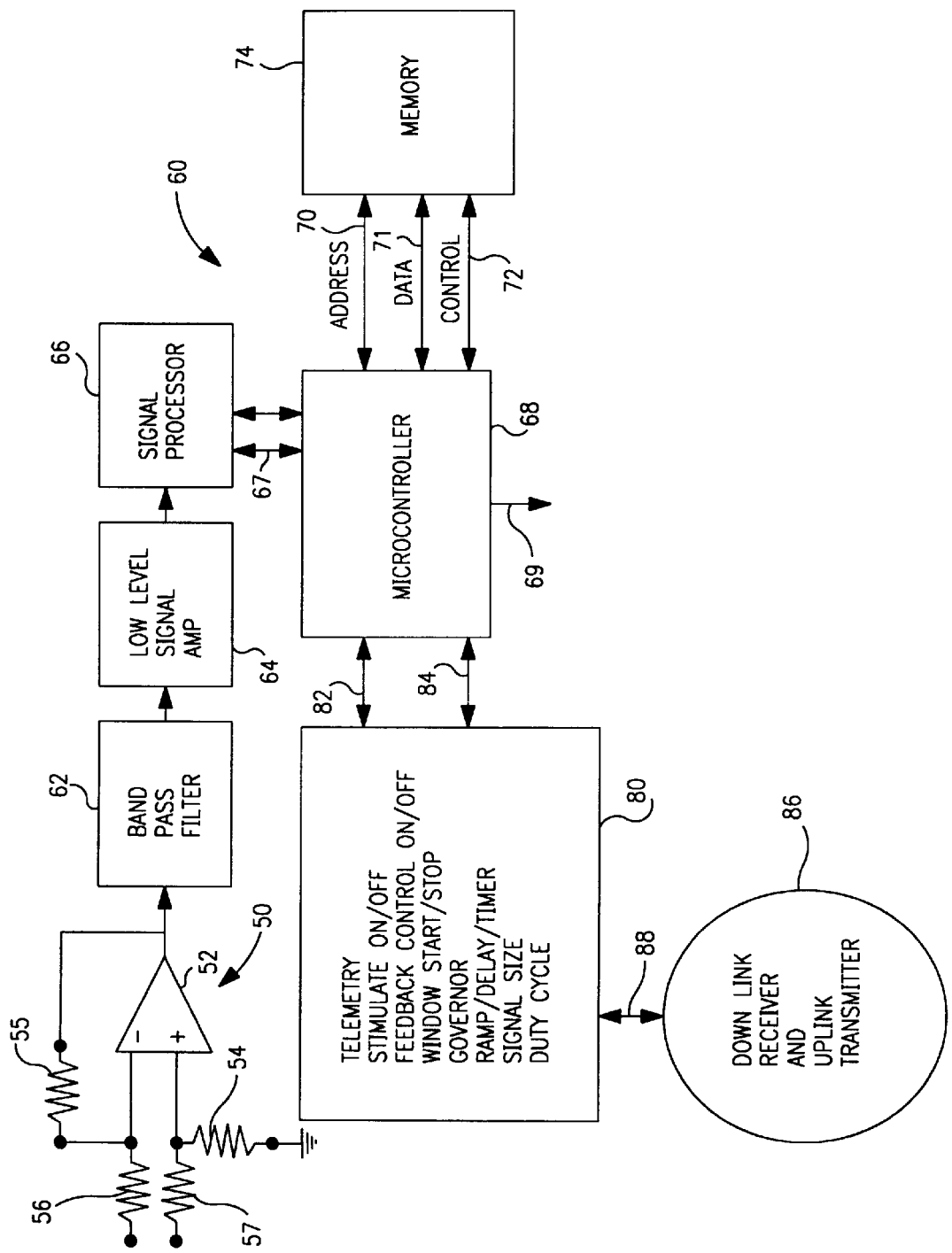
FIG. 5 is a block diagram of the signal processing portion of the present invention.

FIG. 5 discloses the components for processing the sensor signal in accordance with the embodiment of FIG. 2. As shown, these elements reside in implantable device 14A, but may also reside in external component 20 or in signal generator 14 (FIGS. 1 and 3). The output of sensor 30 or 40 is coupled (via telemetry downlink or direct leads) to a conventional differential amplifier 50 comprising an operational amplifier 52 and resistors 54–57 connected as shown. The output of amplifier 50 is connected to a controller 60 basically comprising a band pass filter 62, a low level signal amplifier 64, a signal processor 66, a microcontroller 68, a memory 74, a telemetry unit 80 and a receiver/transmitter unit 86. More specifically, signal processor 66 may take the form of an analog or digital signal microprocessor, or, alternatively, an analog to digital converter. The output of signal processor 66 is conducted over a bus 67 to microcontroller 68. Microcontroller communicates with memory 74 over an address bus 70, a data bus 71 and a control bus 72. An output port of microcontroller 68 produces a control signal on output bus 69. Microcontroller 68 communicates with telemetry unit 80 over buses 82 and 84. Telemetry unit 80 communicates with receiver/transmitter unit 86 via a bus 88. Receiver/transmitter unit 86 provides the clinician a means to adjust parameters of the stimulation, enable or disable the closed-loop feedback control, or adjust the gain of the feedback.

Alternative embodiments are also conceivable. For example, U.S. Pat. No. 5,702,429 (King) discloses other embodiments which may be utilized in the present invention.

Microprocessor 68 is suited to control pulse frequency, amplitude, pulse width, pulse frequency duty cycle, pulse polarity, and/or pulse waveform of the stimulation pulses. The stimulation may also be in the form of a constant or varying stimulation. The pulse frequency is controlled by programming a value to a programmable frequency generator (not shown). The programmable frequency generator provides an interrupt signal to microprocessor 68 when each stimulus pulse is to be generated. The frequency generator may be implemented by model CDP1878 sold by Harris Corporation. The pulse amplitude is programmed to receive the output of a digital to analog converter (not shown). Pulse width is controlled by microprocessor 68 using a programmable pulse width control module (not shown). The pulse width control module provides an enabling pulse of duration equal to the pulse width. Pulses with the selected frequency, amplitude and width characteristics are then delivered from signal generator 14 or 14A through cable 16 and lead 18 to spinal cord 12 or peripheral nerve 45.

Microprocessor 68 executes an algorithm to provide stimulation with closed-loop feedback control. The algorithm serves to process the sensed signal from sensor 30 or 40 and determine whether stimulation should be started, stopped, or altered (by changing pulse amplitude, width, frequency, locus of stimulation, and/or duty cycle). In one embodiment, where sensor 30 or 40 senses equilibrium levels of oxygen in the tissue (for example, a TcPO$_2$ probe), the algorithm operates to ensure that the sensed signal is maintained at or above a certain level. By ensuring that the level of oxygen stays optimally high (above 30 mm Hg), the chances for continued tissue health or healing of lesions are raised. The present invention is preferably designed to allow the feedback signal to be turned off or ignored and operate in an open-loop fashion. This may be at the choice of the patient. For example, the patient may wish to use SCS or PNS for pair including diabetic neuropathy, without having its amplitude controlled by the degree of ischemia Alternatively, it may be desirable to provide a combination of pain relief and improved blood flow. For instance, the patient may wish to stimulate higher in the spinal cord using upper lead electrodes at T9 to control leg pain and lower in spinal cord using lower lead electrodes at T11 to maximize blood flow to the feet. A dual-channel system like the Mattrix® system by Medtronic, Inc. may be used to achieve this purpose.

Figure 6:
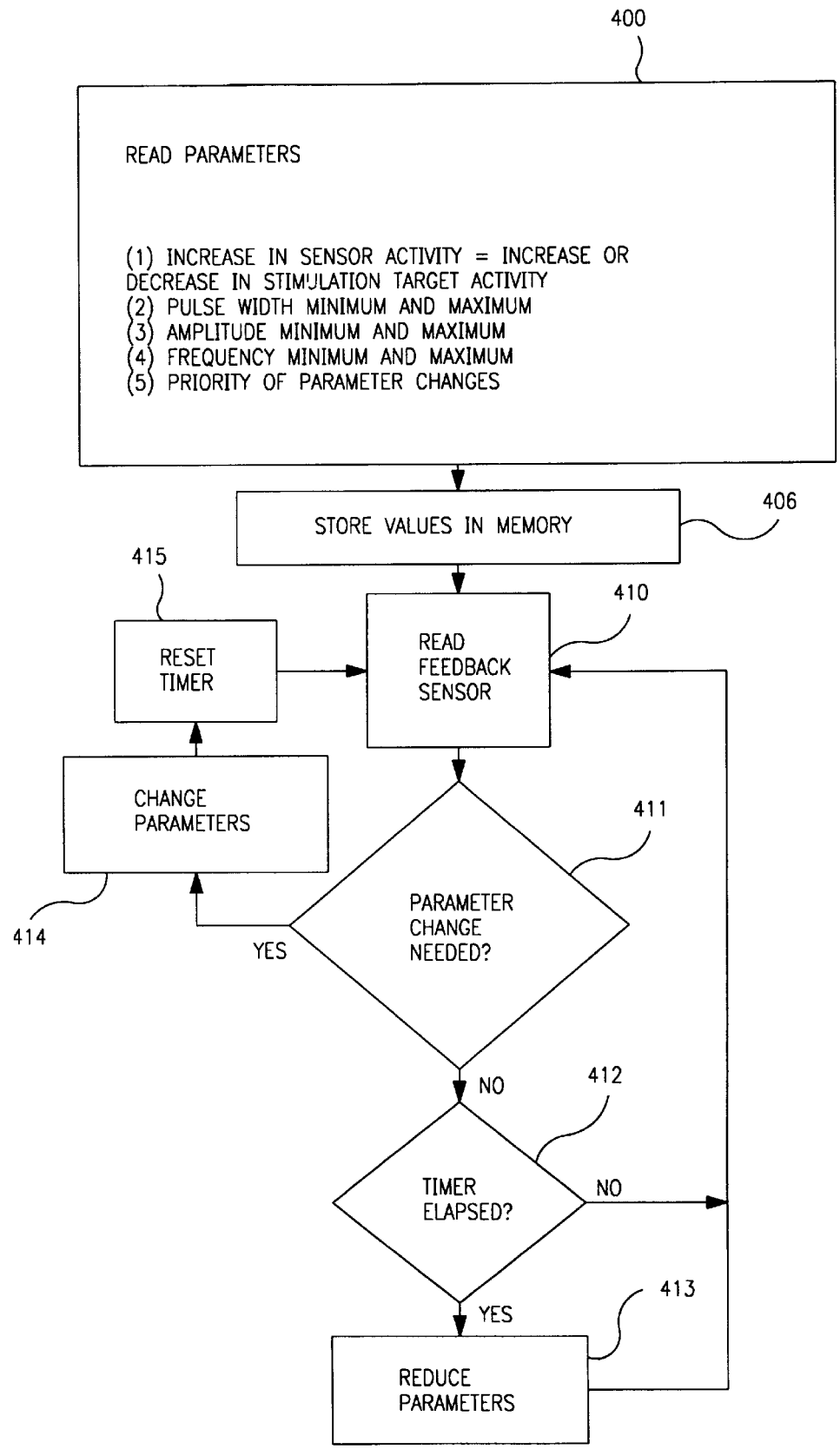
FIGS. 6–8 are flow charts depicting an algorithm for providing the closed-loop feedback control of the SCS or PNS.
Figure 7:
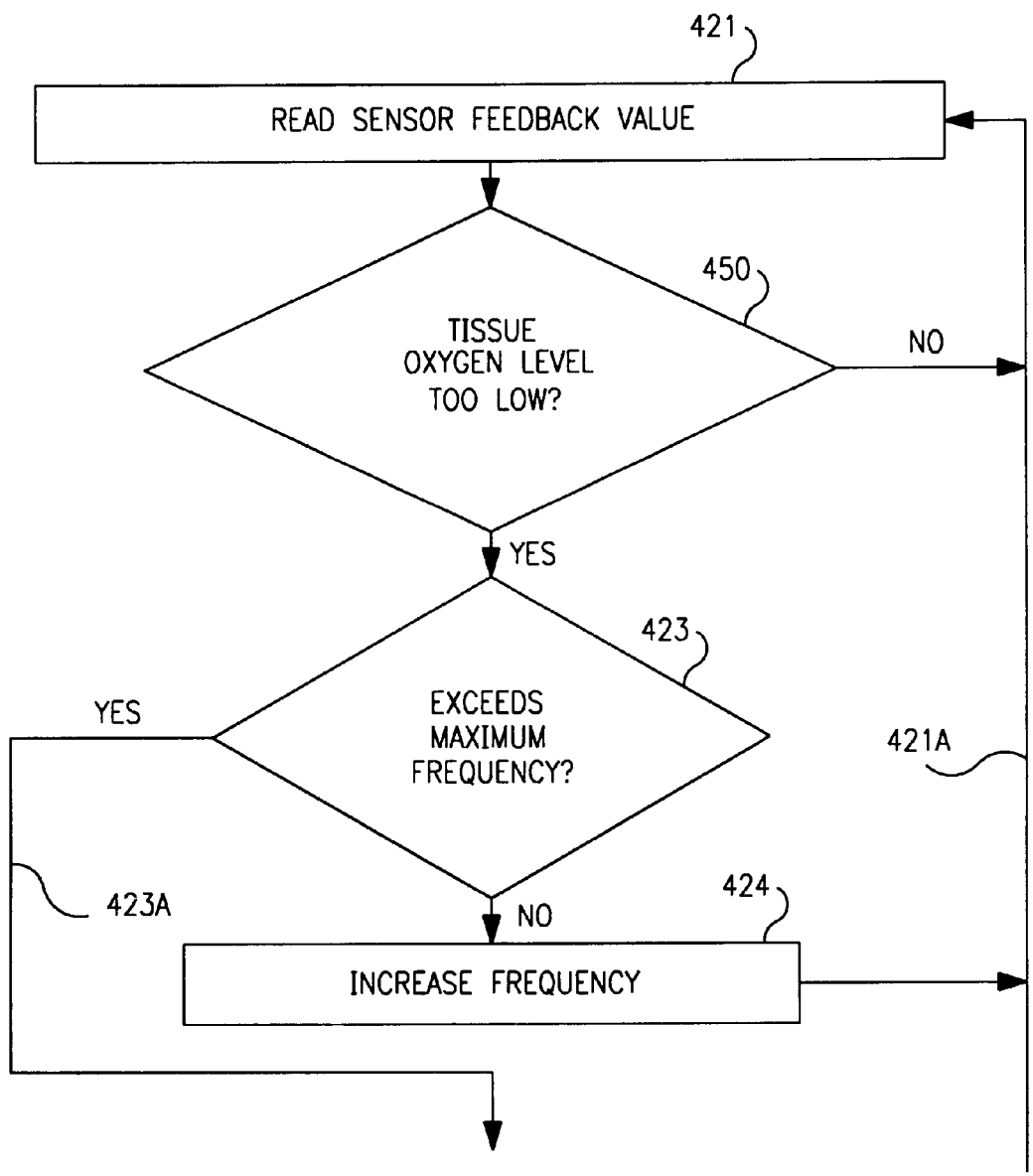
Figure 8:
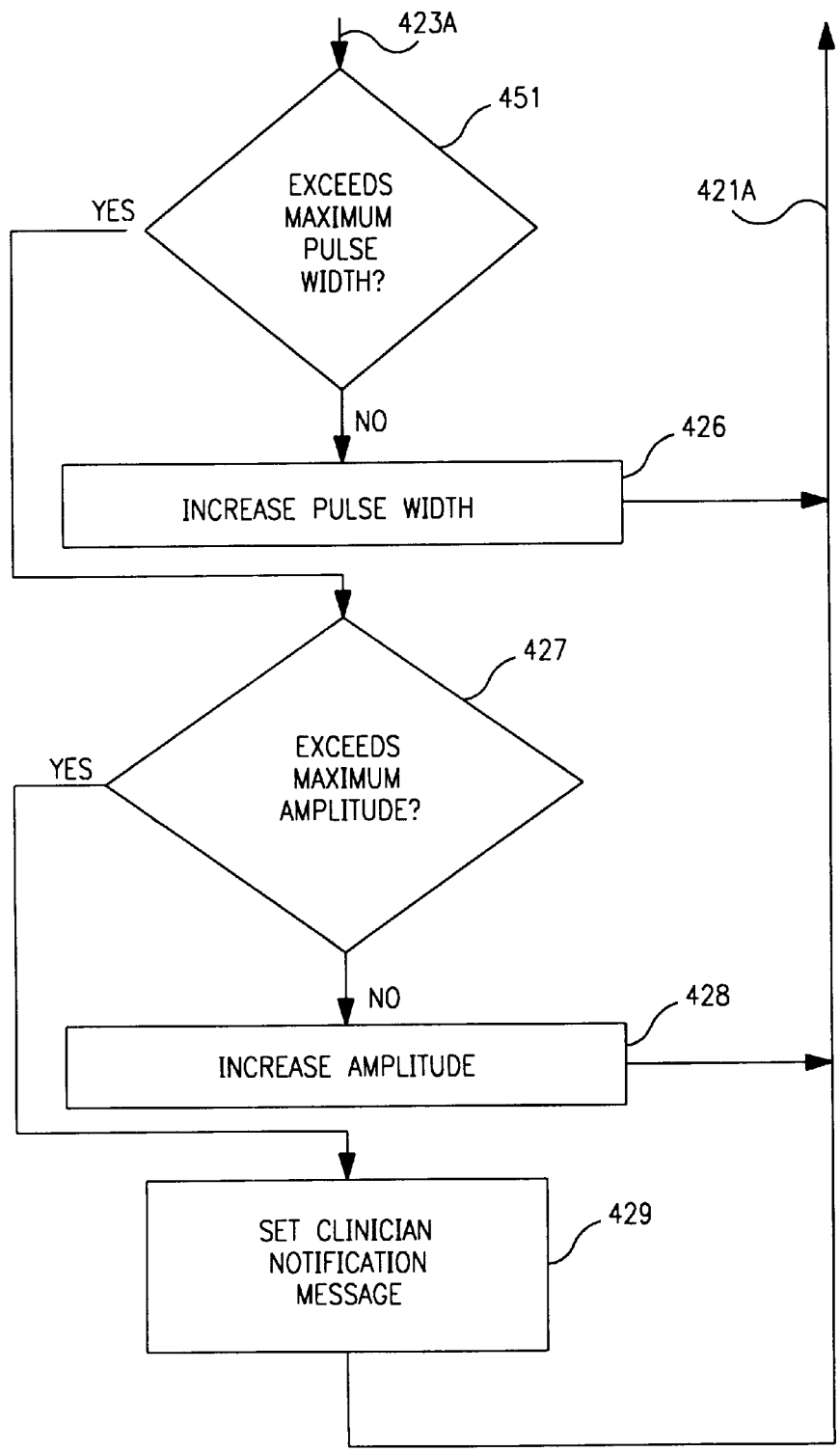

FIGS. 6–8 describe the steps involved in providing closed-loop feedback control in accordance with one embodiment of the present invention. The clinician programs certain key parameters into the memory of component 20 or implanted device 14A. These parameters may be updated subsequently as needed via telemetry or other methods. The clinician must program the range of values for pulse width (step 400(2)), amplitude (step 400(3)) and frequency (step 400(4)) which may be used to optimize the therapy. The clinician may also choose the order in which the parameter changes are made (step 400(5)). Alternatively, the clinician may elect to use default values.

FIGS. 7 and 8 detail steps of the algorithm to make parameter changes in accordance with one embodiment of the present invention. Component 20 or device 14A first reads the feedback sensor signal in step 421 to determine the level of oxygen in the tissue. If the sensor value indicates that the oxygen count is too low (e.g., below 30 mm Hg) (step 450), the algorithm in this embodiment first starts providing SCS or PNS at a predetermined pulse frequency, amplitude, and width. Sensor 30 or 40 continues to monitor the oxygen level and component 20 or generator 14A adjusts the frequency, amplitude, and/or pulse width parameters of the stimulation pulses as required to increase the oxygen level to a desired level. First, the frequency of stimulation in step 424 (FIG. 7) is increased provided this increase does not exceed the preset maximum value set by the physician. Step 423 checks for this condition. If the frequency parameter is not at the maximum the algorithm returns to step 421 through path 421A to monitor the feedback signal from sensor 30 or 40. If the frequency parameter is at the maximum, the algorithm next increases the pulse width in step 426 (FIG. 8), again with the restriction that this parameter has not exceeded the maximum value as checked for in step 451 through path 423A. Not having reached maximum pulse width, the algorithm returns to step 421 to monitor the feedback signal from sensor 30 or 40. Should the maximum pulse width have been reached, the algorithm next increases amplitude in a like manner as shown in steps 427 and 428. In the event that all parameters reach the maximum, a notification message is set in step 429 to be sent by telemetry to the clinician or patient indicating that the system is unable to increase oxygen levels in the tissue. On the other hand, at step 413, if a certain oxygen level is reached, the parameters of stimulation (frequency, width and amplitude) are steadily reduced in the reverse order in which they were increased from steps 424-429 (described below). Eventually, the stimulation may be stopped while still maintaining the requisite oxygen level in the tissue. Monitoring of the oxygen levels, however, continues and the process is restarted when oxygen levels drop below the required minimum. The patient or treating physician may manually adjust the parameters of the stimulation and/or convert the stimulation to an open-loop system where stimulation is provided without regard to the sensor signal.

In closed-loop operation, it is desirable to reduce parameter values for the SCS or PNS to the minimum level needed to maintain the appropriate level blood flow in the tissue. Superimposed on the algorithm just described is an additional algorithm to readjust all the parameter levels downward as far as possible. In FIG. 6, steps 410 through 415 constitute the method to do this. When the parameters are changed, a change timer is reset in step 415. Once this timer has counted a predetermined time interval, the feedback sensor is again sampled (step 410). If tissue physiology has not responded appropriately, the parameters are again changed (step 414). Once the tissue physiology has achieved the preset goals for tissue health or pain reduction, a relaxation timer is consulted (step 412). If the therapy goals continue to be met and the relaxation timer has elapsed, the parameters of stimulation will be reduced (step 413) by a predetermined amount and the sampling process repeats (step 410). The various parameter values will thus be ratcheted down until such time as the sensor values again indicate a need to change them. While the algorithms in FIGS. 6–8 follow the order of parameter selection indicated, other sequences may be programmed by the clinician.

The present invention may be implemented by providing pulses to lead 16 having amplitudes of 0.1 to 20 volts, pulse widths varying from 60 to 1000 microseconds, and repetition rates varying from 5 to 185 Hz or more. Those skilled in the art will appreciate that these ranges may vary depending upon the particular application. For example, repetition rates between 5 and 100 Hz are generally used to excite neurons and above 100 Hz to inhibit neurons. SCS and PNS may use the lower frequency range to cause paresthesia to responsively inhibit the sympathetic outflow. Stimulation of the sympathetic neuronal ganglia or sympathetic neurons may use the higher frequency range to directly inhibit the sympathetic outflow. The appropriate stimulation pulses are generated by generator 14 or 14A based on the computer algorithm shown in FIGS. 6–8 that reads the sensor signal and makes the appropriate analysis. Other stimulation algorithms are also conceivable including the algorithm similar to one disclosed in U.S. Pat. No. 5,702,429 (King).

The algorithm of the present invention may provide any variety of stimulation depending upon the particular needs of the patient. For example, the algorithm may require automatic starting of SCS or PNS when ischemia increases above a threshold level and stopping of SCS or PNS when the ischemia subsides. Alternatively, the algorithm may control SCS or PNS in a gradual, modulated way to adjust stimulation automatically to the degree of ischemia present Alternatively, the algorithm may maintain the tissue physiology (for example, oxygen level) at a constant level such that the pain or side effects remain constant, regardless of patient activity, which can allow the patient to ignore or not be dominated by the potentially annoying symptoms of paresthesia. Alternatively, the algorithm may be programmed to allow the least amount of SCS or PNS to be used, thereby conserving battery life and possibly keeping efficacy high and not destroying nerve cells or preventing the therapy from being ignored or made ineffective by the brain. In the case where sensor 30 or 40 monitors physical activity, the algorithm may activate stimulation when the patient is moving so as to prevent claudication pain. In the case where sensor 30 or 40 senses gravity (for patients with critical limb ischemia), the algorithm may activate stimulation when the patient is lying down.

The method and invention described herein are useful to allow a substantially better control of SCS or PNS for PVD patients. A physiological correlate of the symptoms of ischemia is measured and a feedback signal is generated and used to control the parameters of stimulation. The parameters of the stimulation may vary depending upon the particular needs of the patients. With the improved techniques for SCS or PNS under the present invention, the patient optimizes his/her functional ability, thereby allowing more activities and greater confidence in the performing these activities.

Alternative embodiments are also possible. For example, to save battery power, the circuit shown in FIG. 6 could be arranged so that it is activated only for every tenth or twentieth voltage pulse. Lead 18 may be subdural as well as epidural for SCS or PNS. In certain circumstances, for example, peripheral nerve stimulation, control of polarities and active electrodes might be done based on feedback signals from sensor 30 or 40.

Referring back to FIG. 5, controller 60 can be turned on or off (for example by telemetry) in order to provide stimulation of nerve fibers adjacent lead 18. In addition, feedback control can be turned on or off. When feedback control is turned on, differential amplifier 50, band pass filter 62, amplifier 64, signal processor 66, microcontroller 6S and memory 74 are switched from an inactive to an active state. Additionally, a maximum safe amplitude or pulse width for stimulation may be preset to keep the maximum paresthesia comfortable. The maximum amplitude or pulse width of the pulses should be determined empirically with each patient. The components of FIG. 5 may also provide a ramp/delay/timer feature which allows the automatic feedback controller to start or stop gradually, or to start or stop at a selected time. Other stimulation features used at present (duty cycle, modulation) may also still be available with or without feedback amplitude control.

The signal size may also be allowed to be adjusted automatically when the stimulation system is first turned on, by gradually increasing the amplitude of pulses until a prior stored value of feedback signal is produced. Memory unit 74 can store prior parameters of stimulation, polarities, or size of recorded feedback signal. Microcontroller 68 can be programmed to perform the foregoing functions described by those skilled in the art.

By using the foregoing techniques for spinal cord stimulation, PVD patients may be treated to increase blood flow in the limbs, thereby reducing suffering from ischemic pain in the limbs. Advantageously, the present invention may be used to control blood flow to a patch of tissue, for example a skin dermatome, on the trunk of the patient which may have too little or too much blood flow, to alleviate a neuropathic or ischemic pain due to post-herpetic neuralgia or complex regional pain syndrome (CRPS). Alternatively, if internal organs have a loss of blood flow due to sympathetic neuronal over-activity, lead 18 may be placed at optimal spinal cord locations or in the sympathetic ganglia that project to those organs or along nerves that project to those organs. Those skilled in that art will recognize that the preferred embodiments may be altered or amended without departing from the true spirit and scope of the invention, as defined in the accompanying claims.

I claim:

1. A system for therapeutically treating peripheral vascular disease in the limb of a patient comprising:
    (a) a signal generator;
    (b) at least one implantable lead coupled to the signal generator and adapted to stimulate neural tissue in at least one predetermined site;
    (c) a sensor for generating a signal related to the extent of vascular blood flow in said limb; and
    (d) a processor responsive to the sensor for adjusting at least one parameter of the stimulation by the lead to treat said peripheral vascular disease.

2. A system as claimed in claim 1, wherein the lead stimulates a spinal cord.

3. A system as claimed in claim 1, wherein the lead stimulates a peripheral nerve.

4. A system as claimed in claim 3, wherein the peripheral nerve is a sciatic nerve.

5. A system as claimed in claim 1, wherein the lead stimulates a neuronal ganglia.

6. A system as claimed in claim 1, wherein the lead stimulates sympathetic system neurons intrinsic to blood vessels or organs.

7. A system as claimed in claim 1, wherein the lead includes at least one stimulating electrode.

8. A system as claimed in claim 1, wherein the sensor monitors a physiological characteristic of a body, the physiological characteristic being selected from the group consisting of skin oxygen, blood oxygen saturation, skin temperature, blood flow rate, muscle oxygen level, tissue temperature, muscle lactic acid build-up, muscle activity, nerve activity, muscle EMG, brain EEG and sympathetic nervous tissue activity.

9. A system as claimed in claim 1, wherein the sensor monitors gravity direction.

10. A system as claimed in claim 1, wherein the sensor is a motion detector.

11. A system as claimed in claim 1, wherein the sensor is an implantable sensor.

12. A system, as claimed in claim 1, wherein the processor includes a microprocessor.

13. A system, as claimed in claim 1, wherein the processor includes an electrical filter.

14. A system as claimed in claim 1, wherein the processor utilizes an algorithm for processing the signal from the sensor.

15. A system as claimed in claim 1, wherein the parameter is selected from the group consisting of pulse amplitude, pulse width, pulse frequency, pulse frequency duty cycle, pulse polarity, and pulse waveform.

16. A system, as claimed in claim 1, further comprising a telemetry downlink to provide communication between the sensor and the processor.

17. A system as claimed in claim 1, further comprising a telemetry downlink to provide communication between the processor and the signal generator.

18. A system as claimed in claim 1, further comprising a single housing that contains the processor and signal generator.

19. A system as claimed in claim 1, wherein the lead stimulates a peripheral nerve or a sympathetic neuronal ganglia and the signal generator provides pulses having a repetition rate of at least 100 Hz.

20. A method of therapeutically treating peripheral vascular disease by means of a signal generator and at least one implantable lead having a proximal end and a stimulation portion comprising the steps of:
    (a) implanting the lead near neural tissue of a body so that the stimulation portion lies adjacent a predetermined treatment site;
    (b) coupling the proximal end of the lead to the signal generator;
    (c) operating the signal generator to stimulate the predetermined site and to increase vascular blood flow to an area of the body suffering from peripheral vascular disease;
    (d) generating a sensor signal related to the extent of vascular blood flow, and
    (e) regulating the stimulation in response to the sensor signal to provide a predetermined level of blood flow.

21. A method as claimed in claim 20, wherein the step of implanting the lead includes the step of positioning the lead to stimulate neural tissue in a spinal cord.

22. A method as claimed in claim 20, wherein the step of implanting the lead includes the step of positioning the lead to stimulate neural tissue in a peripheral nerve.

23. A method as claimed in claim 20, wherein the step of implanting the lead includes the step of positioning the lead to stimulate neural tissue along a surface of a blood vessel or an organ.

24. A method as claimed in claim 20, wherein the step of implanting the lead includes the step of positioning the lead to stimulate neural tissue in a sympathetic neuronal ganglia.

25. A method as claimed in claim 20, wherein the step of implanting the lead includes the step of positioning the lead to stimulate neural tissue in a sciatic nerve.

26. A method as claimed in claim 20, further comprising the step of monitoring a physiological characteristic of a body, the physiological characteristic being selected from the group consisting of skin oxygen, blood oxygen saturation, skin temperature, blood flow rate, muscle oxygen level, tissue temperature, muscle lactic acid build-up, muscle activity, nerve activity, muscle EMG, brain EEG, and sympathetic nervous tissue activity.

27. A method as claimed in claim 20, wherein the stimulation comprises pulses having a repetition rate of 5 to 185 Hz.

28. A method as claimed in claim 20, wherein the stimulation comprises pulses having a pulse width varying from 60 to 1000 microseconds.

29. A method as claimed in claim 20, wherein the stimulation comprises pulses having an amplitude of 0.1 to 20.0 Volts.

30. A method as claimed in claim 20, further comprising the step of surgically implanting a signal generator in the body.

31. A method as claimed in claim 20, wherein the step of regulating includes the step of executing a control algorithm.

32. A method as claimed in claim 20, wherein the step of generating the sensor signal comprises the steps of sensing activity of a sympathetic nervous system.

33. A method as claimed in claim 20, wherein the step of implanting the lead includes the step of positioning the lead to stimulate a peripheral nerve or a sympathetic neuronal ganglia and the step of operating the signal generator includes the step of providing pulses having a repetition rate of at least 100 Hz.

34. A method of therapeutically treating ischemic pain by means of a signal generator and at least one implantable lead having a proximal end and a stimulation portion comprising the steps of:
   (a) implanting the lead near neural tissue of a body so that the stimulation portion lies adjacent a predetermined treatment site;
   (b) coupling the proximal end of the lead to the signal generator;
   (c) operating the signal generator to stimulate the predetermined site and to increase vascular blood flow to an area of the body that is causing the ischemic pain;
   (d) generating a sensor signal related to the extent of ischemic pain suffered by a patient; and
   (e) regulating the stimulation in response to the sensor signal to provide a predetermined level of blood flow and reduce the ischemic pain suffered by the patient.

35. A method as claimed in claim 34, wherein the ischemic pain is in a limb of the patient.

36. A method as claimed in claim 34, wherein the ischemic pain is in an organ of the patient.

37. A method as claimed in claim 36, wherein the organ is a portion of skin.

38. A method as claimed in claim 34, wherein the step of implanting the lead includes the step of positioning the lead to stimulate a peripheral nerve or a sympathetic neuronal ganglia and the step of operating the signal generator includes the step of providing pulses having a repetition rate of at least 100 Hz.

39. A method of therapeutically maintaining a constant blood flow rate to a portion of a body of a patient by means of a signal generator and at least one implantable lead having a proximal end and a stimulation portion comprising the steps of:
   (a) implanting the lead near neural tissue of a body so that the stimulation portion lies adjacent a predetermined treatment site;
   (b) coupling the proximal end of the lead to the signal generator;
   (c) operating the signal generator to stimulate the predetermined site;
   (d) generating a sensor signal related to the extent of blood flow in the portion of the patient's body; and
   (e) regulating the stimulation in response to the sensor signal to maintain a predetermined level of blood flow to the portion of the patient's body.

40. A method as claimed in claim 39, wherein the step of implanting the lead includes the step of positioning the lead to stimulate a peripheral nerve or a sympathetic neuronal ganglia and the step of operating the signal generator includes the step of providing pulses having a repetition rate of at least 100 Hz.

41. A system for therapeutically treating peripheral vascular disease comprising:
   (a) a signal generator;
   (b) means responsive to the signal generator for stimulating neural tissue to increase blood flow to an area of a body suffering from peripheral vascular disease;
   (c) a sensor for generating a signal related to the extent of vascular blood flow; and
   (d) means responsive to the sensor for adjusting at least one parameter of the stimulation by the lead.

42. A system as claimed in claim 41, wherein the means responsive to the signal generator stimulates a peripheral nerve or a sympathetic neuronal ganglia and the signal generator provides pulses having a repetition rate of at least 100 Hz.

43. A system for reducing sympathetic neuronal activity in a portion of a patient's body comprising:
   (a) a signal generator;
   (b) at least one implantable lead coupled to the signal generator and adapted to stimulate neural tissue that project to the portion of the patient's body to increase blood flow;
   (c) a sensor for generating a signal related to the extent of blood flow in the portion of the patient's body; and
   (d) a processor responsive to the sensor for adjusting at least one parameter of the stimulation by the lead.

44. A method of reducing sympathetic neuronal activity in a portion of a patient's body by means of a signal generator and at least one implantable lead having a proximal end and a stimulation portion comprising the steps of:
   (a) implanting the lead near neural tissue of a body so that the stimulation portion lies adjacent neural tissue that project to the portion of the patient's body;
   (b) coupling the proximal end of the lead to the signal generator;
   (c) operating the signal generator to stimulate the neural tissue and to increase vascular blood flow to the portion of the patient's body;
   (d) generating a sensor signal related to the extent of vascular blood flow; and
   (e) regulating the stimulation in response to the sensor signal to provide a predetermined level of blood flow to the portion of the patient's body.

45. A method as claimed in claim 44, wherein the step of implanting the lead includes the step of positioning the lead to stimulate neural tissue selected from the group consisting of a spinal cord, sympathetic ganglia that project to the portion of the patient's body, and nerves that project to the portion of the patient's body.

46. A method as claimed in claim 44, wherein the step of regulating includes the step of executing a control algorithm.

47. A method as claimed in claim 44, wherein the portion of the patient's body is an organ and the step of regulating provides a predetermined level of blood flow to the organ.

* * * * *

UNITED STATES PATENT AND TRADEMARK OFFICE
CERTIFICATE OF CORRECTION

PATENT NO.: 6,058,331

DATED: May 2, 2000

INVENTOR(S): Gary W. King

It is certified that error appears in the above-identified patent and that said Letters Patent is hereby corrected as shown below:

at column 1, line 35 reads "tanscutaneous" and should read - -transcutaneous- - at column 3, line 18 reads"...painfull" and should read - -...painful- - at column 3, line 46 reads "cord In ..." and should read - -cord. In ...- - at column 8, line 56 reads "...of ischemia" and should read - -...of ischemia.- - at column 10, line 32 reads "...microcontroller 65" and should read - -...microcontroller 68- - at column 11, line 6 reads "...microcontroller 65" and should read --...microcontroller 68--

Signed and Sealed this

Twenty-fourth Day of April, 2001

Attest:

NICHOLAS P. GODICI

Attesting Officer

Acting Director of the United States Patent and Trademark Office